(12) United States Patent
Rojas Martinez et al.

(10) Patent No.: US 11,452,482 B2
(45) Date of Patent: Sep. 27, 2022

(54) PORTABLE DEVICE, SYSTEM AND METHOD FOR MEASURING ELECTROMYOGRAPHIC SIGNALS OF A USER

(71) Applicant: UNIVERSITAT POLITÈCNICA DE CATALUNYA, Barcelona (ES)

(72) Inventors: Mónica Rojas Martinez, Barcelona (ES); Miguel Angel Mañanas Villanueva, l'Hospitalet de Llobregat (ES)

( * ) Notice: Subject to any disclaimer, the term of this patent is extended or adjusted under 35 U.S.C. 154(b) by 541 days.

(21) Appl. No.: 15/746,629

(22) PCT Filed: Jul. 22, 2016

(86) PCT No.: PCT/IB2016/001040
§ 371 (c)(1),
(2) Date: Jan. 22, 2018

(87) PCT Pub. No.: WO2017/013486
PCT Pub. Date: Jan. 26, 2017

(65) Prior Publication Data
US 2018/0206782 A1 Jul. 26, 2018

(30) Foreign Application Priority Data

Jul. 23, 2015 (EP) .................................. 15380033

(51) Int. Cl.
*A61B 5/00* (2006.01)
*A61B 5/296* (2021.01)
(Continued)

(52) U.S. Cl.
CPC ............ *A61B 5/486* (2013.01); *A61B 5/0002* (2013.01); *A61B 5/296* (2021.01); *A61B 5/389* (2021.01);
(Continued)

(58) Field of Classification Search
None
See application file for complete search history.

(56) References Cited

U.S. PATENT DOCUMENTS 8,718,742 B2     5/2014   Beck et al.
2005/0275416 A1* 12/2005  Hervieux ........... A41D 13/1281
                                                        324/663
(Continued)

FOREIGN PATENT DOCUMENTS

CN       103190905      12/2014
CN       102961132      2/2015
(Continued)

OTHER PUBLICATIONS

Rojas-Martinez et al: "Identification of isometric contractions based on High Density EMG maps, Jounal of Electromyography and Kinesiology 2012".
(Continued)

*Primary Examiner* — Patrick Fernandes
(74) *Attorney, Agent, or Firm* — Eugenio J. Torres-Oyola; Victor M. Rodriguez-Reyes; Rafael Rodriguez-Reyes

(57) ABSTRACT

The device comprises: a first support layer (C1) having detection means including several electrodes (11) arranged, in use, in contact with the skin of a user on at least one muscle, or part thereof, and configured for acquiring a plurality of electromyographic signals, said first support layer (C1) being mechanically and electrically attached in a detachable manner to a second support layer (C2); and said second support layer (C2) which includes electronic means (BE) configured for performing the conditioning of said acquired electromyographic signals, conversion thereof to a digital format and transmission through a communication channel (26) to a master electronic unit (27), wherein said master electronic unit (27) is configured for controlling said electronic means (BE) and to further transmit the received
(Continued)

conditioned and digitized electromyographic signals to a control unit (30) for monitoring thereof.

6 Claims, 6 Drawing Sheets

(51) Int. Cl.
*A61B 5/389* (2021.01)
*A61B 5/1455* (2006.01)

(52) U.S. Cl.
CPC ........ *A61B 5/6804* (2013.01); *A61B 5/14552* (2013.01); *A61B 5/6823* (2013.01); *A61B 5/6824* (2013.01); *A61B 5/742* (2013.01); *A61B 5/7405* (2013.01); *A61B 2560/045* (2013.01); *A61B 2560/0443* (2013.01); *A61B 2562/046* (2013.01)

(56) References Cited

U.S. PATENT DOCUMENTS

| | | | |
|---|---|---|---|
| 2006/0173364 A1* | 8/2006 | Clancy | A61B 5/04 600/485 |
| 2007/0265543 A1 | 11/2007 | VanSickle et al. | |
| 2010/0162832 A1* | 7/2010 | Brauers | A61B 5/103 73/862.626 |
| 2010/0317958 A1* | 12/2010 | Beck | A61B 5/0006 600/391 |
| 2013/0030259 A1* | 1/2013 | Thomsen | A61B 5/02028 600/301 |
| 2013/0041235 A1* | 2/2013 | Rogers | A61B 5/1107 600/306 |
| 2013/0068804 A1 | 3/2013 | Tweedie | |
| 2013/0281814 A1* | 10/2013 | Tilt | A61B 5/282 600/382 |
| 2013/0317648 A1 | 11/2013 | Assad | |
| 2014/0070957 A1* | 3/2014 | Longinotti-Buitoni | A61B 5/6804 340/870.01 |
| 2016/0007927 A1* | 1/2016 | Fuketa | A61B 5/6832 29/592.1 |
| 2016/0066854 A1* | 3/2016 | Mei | H04B 5/0031 361/749 |
| 2018/0036531 A1* | 2/2018 | Schwarz | G16H 20/30 |

FOREIGN PATENT DOCUMENTS

| | | |
|---|---|---|
| CN | 103393420 | 6/2015 |
| DE | 102008024972 | 12/2009 |
| EP | 2335570 | 6/2011 |
| ES | 2346174 | 10/2010 |
| WO | 2007/141680 | 12/2007 |
| WO | 2008/017921 | 2/2008 |
| WO | 20130068804 | 5/2013 |

OTHER PUBLICATIONS

Rojas-Martinez et al: "High-density surfaces EMG maps from upper-arm and forearm muscles, Journal of NeuroEngineering and Rehabilitation 2012".

Hamid R. Marateb et al.: "Outlier detection in high-density surface electromyographic signals".

International Search Report and written opinion dated Nov. 25, 2016 for PCT/IB2016/001040.

IPRP issued on Sep. 4, 2017 for PCT/IB2016/001040.

* cited by examiner (A)

(B)

PORTABLE DEVICE, SYSTEM AND METHOD FOR MEASURING ELECTROMYOGRAPHIC SIGNALS OF A USER

RELATED APPLICATIONS

This application is the US national phase application of international application number PCT/IB2016/001040, filed 22 Jul. 2016, which designates the US and claims priority to European application EP15380033.9 filed 23 Jul. 2015, the contents of each of which are hereby incorporated by reference as if set forth in their entireties.

FIELD OF THE ART

The present invention generally relates to the field of electromyography. In particular, the invention relates to a portable device for measuring electromyographic signals (or high-resolution electromyographic signals, HR-EMG) of a user through the integration in said portable device of sensors and electronic circuits in a bilayer flexible sheet support, providing a large number of measurement points for measuring the electromyographic signals.

The invention also provides a system and a method for measuring the electromyographic signals of a user using the proposed portable device.

BACKGROUND OF THE INVENTION

Patent document US-A1-20130317648 discloses a system and method for measuring muscle action and gestures in order to control robotic devices or machines. The system can be used by a user (for example, in a sleeve) and includes several electromyography sensors and at least one inertial sensor. The power, processing and transmission circuits can be built into the same sleeve and the control data can be transmitted wirelessly or in a guided manner (for example, through wire) to an external device.

Patent document WO-A1-2013068804 discloses a device for measuring electromyographic signals, suitable for receiving, using multiple channels, several electromyographic signals detected with several electrodes arranged on a user. The device comprises a conditioning circuit, a conversion circuit, transmission circuit for transmission to a central control unit and an external casing suitable for housing said circuits. The conditioning circuit can be assembled modularly by establishing a cascade connection with one or more conditioning circuits, similarly, the conversion circuits can also change the number of electromyographic channels. The conditioning and conversion circuits can overlap one another such that the dimensions of the casing containing same can be limited so that they can be used by the user.

Patent document CN-A-103393420 discloses another device for measuring electromyographic signals formed by a high-density flexible electrode assembly and a signal conditioning circuit for the array. The signal conditioning circuit comprises a high-density flexible electrode array and a filter for the amplification thereof. The electrode array collects surface potentials in the position corresponding to the electrodes, and an operational amplifier or an instrumental amplifier arranged on a flexible plate performs impedance transformation or first-stage amplification. The high-density flexible electrode array can acquire surface potentials of the skin of a user with high quality and low noise level, even in uneven areas.

Patent document WO-A2-2008017921 discloses a system for acquisition of bioelectric signals envisaging the use of at least a first detection electrode, placed in use on a portion of the skin surface to detect bioelectric signals, and an electrical connection structure for connecting the first detection electrode—to an electronic device for processing, of the bioelectric signals. The electrical connection structure has a first removable connection element, based on magnetic interaction. Both the first detection electrode and the removable connection element are plated with a conductive material such as Ag or AgCl. The acquisition system is provided with an array of detection electrodes incorporated into an electrode support, and the electrical connection structure has a corresponding array of removable connection elements incorporated into a magnet support; each removable connection element is placed, in use, corresponding to a respective detection electrode and is designed to magnetically interact with such detection electrode. Unlike present invention, the system disclosed in this patent application does not perform digitalization of the detected bioelectric signals near the detection electrodes but it only performs amplification of the detected bioelectrical signals to improve signal to noise ratio. By performing the digitalization of the detected bioelectrical signals near the detection electrodes, degradation of the detected bioelectrical signals due to its transmission over the cable is avoided. Besides, the system of this patent application does not includes a master electronic unit being able to control one or more electronic means, that is a master electronic unit for controlling conditioning, digitalization and also transmission of the detected bioelectrical signals, neither envisages a modular structure of the electronic connections of the system to increase detection area and to exchange analog and digitized information from acquired EMG signals.

Other devices and/or methods for measuring electromyographic signals are also described in patent documents: CN-102961132 and/or CN-A-103190905.

However, at present there is no known portable electromyographic signal measuring device formed by a flexible sheet support comprising two different support layers, a first sheet support comprising detection means including several electrodes for acquiring electromyographic signals, and one or more second sheet supports, mechanically and electrically attached in a detachable manner to said first sheet support, including electronic means for conditioning, digitizing and transmitting said electromyographic signals to a master electronic unit, the latter further transmitting the received signals to a control unit for monitoring thereof.

Likewise, a device capable of covering muscle areas (more than one muscle) of different amplitude based on a peripheral mechanical and electrical coupling of two or more portable devices such as the one proposed is not known in the state of the art either.

BRIEF DESCRIPTION OF THE INVENTION

According to a first aspect, the present invention provides a portable device for measuring electromyographic signals (or high-resolution electromyographic signals, HR-EMG) of a user. The portable device comprises a first support layer including detection means including several electrodes which can be arranged, in use, in contact with the skin of the user on at least one muscle, or part thereof, for acquiring a plurality of electromyographic signals.

The portable device also comprises one or more second support layers which can be mechanically and electrically attached in a detachable manner by means of electro-conductive couplings (for example, a button, a clip, etc.) to said first support layer. Each second support layer comprises electronic means configured for performing the conditioning (amplification, time filtering and optionally spatial filtering, and also optionally multiplexing) of said plurality of acquired electromyographic signals, conversion of the signals to a digital format and transmission of the conditioned and digitized electromyographic signals through a communication channel to a master electronic unit of the portable device (UB).

The master electronic unit is configured to control the electronic means of the one or more second support layers and also configured to transmit the received conditioned and digitized electromyographic signals to a control unit for monitoring thereof. To that end, the master electronic unit can be included in a second support layer, forming part of this second support layer, or can also be shared by a plurality of interconnected second support layers.

For the embodiments of having more than one second support layers, some of them can be mechanically and electronically attached to each other (i.e. interconnected) to increase the detection area and to exchange both analog and digitized information via electrical connectors and via said communication channel. As said before, in the case of having interconnected second support layers, the master electronic unit will be shared by them and configured for controlling each one of the electronic means included in each one of the interconnected second support layers.

In an embodiment, the electronic means of a second support layer that is mechanically and electrically attached to another second support layer is configured to control some of adjacent electrodes of the first support layer attached to this another second support layer during the performing of said conditioning, for instance when differential and/or laplacian records are desired.

The portable device allows detaching the two support layers, first and second, making the washing and/or disinfection thereof easier and likewise allowing treatment and digitalization of the acquired electromyographic signals to be performed in the portable device itself, close to the mentioned detection means, degradation and possible interferences in the acquired electromyographic signals due to noise and/or other contaminations and the structural complexity of the detection means thus being minimized, for example.

The first support layer in an embodiment comprises a breathable, waterproof fabric, and the second support layer comprises a fabric with semiconductive properties in certain waterproof and breathable portions.

In one embodiment, the electrodes are placed in the first support layer in a matricial form. In other embodiments, the electrodes are placed in a laplacian form or circular form.

In one embodiment, the portable device incorporates in its periphery coupling elements, which are also electro-conductive, for coupling to one or more portable devices, thereby widening the whole covered muscle area or allowing covering different muscle areas. The control unit in this case is configured to monitor the electromyographic signals received from the master electronic units of all the coupled portable devices.

In one embodiment, in particular for the case in which only one second support layer is mechanically and electrically attached to the first support layer, the proposed portable device is incorporated in or attached to a wearable item of clothing, for example, an armband, strap or sleeve for an upper limb of the body of the user, an abdominal band, a strap or stocking for a lower limb of the body of the user, or a shirt with a tight-fitting part, for fixing to a treatment area.

In another embodiment, in particular for the case in which more than one second support layers are mechanically and electrically attached to the first support layer, the first support layer is incorporated in or attached to a wearable item of clothing including an armband, a strap for an upper or lower limb of the body of the user, an abdominal band, a trousers or a shirt, and the second support layers are configured to be attached to different parts of said wearable item of clothing selected depending on the muscle or muscles from which the electromyographic signals have to be measured according to the interest of the exercise carried out by the user.

In one embodiment, the mentioned control unit for monitoring the electromyographic signals is an electronic unit positioned in the second support layer which receives said electromyographic signals by means of a conductive plane or a wired technology.

In another embodiment, the control unit is remote with respect to the proposed portable device(s), receiving said electromyographic signals through a guiding or wireless means (for example, using Bluetooth or infrared technology, among others). In this case, the control unit preferably comprises a computing device with one or more processors to further perform the processing of the received electromyographic signals.

The proposed portable device can also include one or more batteries for electrically powering the different electronic components included in the second support layer of the proposed portable device. Besides, the battery or batteries make the portable device safer for the user as the device doesn't have to be directly plugged to work.

The control unit can also include warning means for emitting indications associated with changes in a prefixed muscle pattern, based at least on muscle co-activation or fatigue indices obtained during the processing of the electromyographic signals in time, frequency or spatial domain.

In one embodiment, the mentioned communication channel comprises a data bus. Alternatively, in another embodiment said communication channel comprises a conductive plane formed by an electro-resistive track extended on a portion of the second support layer.

According to a second aspect, the present invention also provides a system for measuring electromyographic signals of a user, comprising one or more portable devices, as the ones previously described, and a control unit configured to at least monitor electromyographic signals received from the master electronic unit or units of the one or more portable devices.

The one or more portable devices can be mechanically and electrically coupled by means of electro-conductive coupling elements located in the periphery thereof, so allowing to cover different muscles of a same body part, e.g. the biceps and triceps, or can be separated to each other and located on different parts of the body of the user (e.g. one placed on a muscle of the left arm and another on a muscle of the right arm).

According to yet another aspect, the present invention provides a method for measuring electromyographic signals of a user. The method comprises mechanically and electrically attaching a first support layer comprising detection means including several electrodes in a detachable manner by means of electro-conductive couplings to a second support layer, the attachment of the two support layers forming a portable device (UB); fixing said portable device on at least one muscle, or part thereof, of a user, the first support layer being in contact, in use, with the skin of the user; acquiring, by said several electrodes, a plurality of electromyographic signals while the user is performing an exercise; conditioning, by electronic means included in the second support layer, by amplification and filtering (time and optionally spatial) the plurality of acquired electromyographic signals; converting, by the electronic means, the electromyographic signals to a digital format; transmitting, by the electronic means, the conditioned and digitized electromyographic signals through a communication channel to a master electronic unit of the portable device; controlling, by said master electronic unit operation of the electronic means and further transmitting the received conditioned and digitized electromyographic signals to a control unit; and monitoring and processing, by the control unit including at least one processor and at least one memory, the received electromyographic signals, said processing comprising calculation of one or more muscle activation maps and/or calculation of different indices relating to muscle coordination and/or activation and/or fatigue of said user in relation to the fixed muscle, or part thereof.

In one embodiment, the method comprises mechanically and electrically attaching in a detachable manner a plurality of second support layers to the first support layer, the master electronic unit comprising controlling operation of each one of the electronic means included in said plurality of second support layers.

In one embodiment, the processing result is shown to the user at the time of performing the exercise thereby allowing the user to control the exercise while (s)he is performing said exercise. For example, the results can be displayed (shown) to the user by means of a display, either of the control unit itself or of a computing device of the user, which is remote with respect to the control unit, such as a smartphone or tablet, among others.

In another embodiment, the processing result, prior to being displayed (shown) to the user, is stored in said memory of the control unit, for subsequently preparing clinical evaluation reports and/or monitoring the performance of the exercise, for example, allowing the review thereof by at least a second user (medical and/or healthcare staff, personal trainer, etc.).

The present invention is particularly applicable in various fields, such as neurophysiology, rehabilitation, physiotherapy, ergonomics and/or sports, among others, in which the muscle response of a user both in static situations and situations in which movement is present must be measured.

BRIEF DESCRIPTION OF THE DRAWINGS

The foregoing and other features and advantages will be better understood based on the following detailed description of several merely illustrative and non-limiting embodiments in reference to the attached drawings, in which:

FIG. 4*a* illustrates a profile view of the arrangement of the two support layers forming the portable device; in this case, the communication channel of the portable device comprises a conductive plane formed by an electro-resistive track. FIG. 4*b* illustrates a plan view of the arrangement of the electromyography sensors that would be arranged in contact with the skin of the user;

DETAILED DESCRIPTION OF SEVERAL EMBODIMENTS

Figure 1:
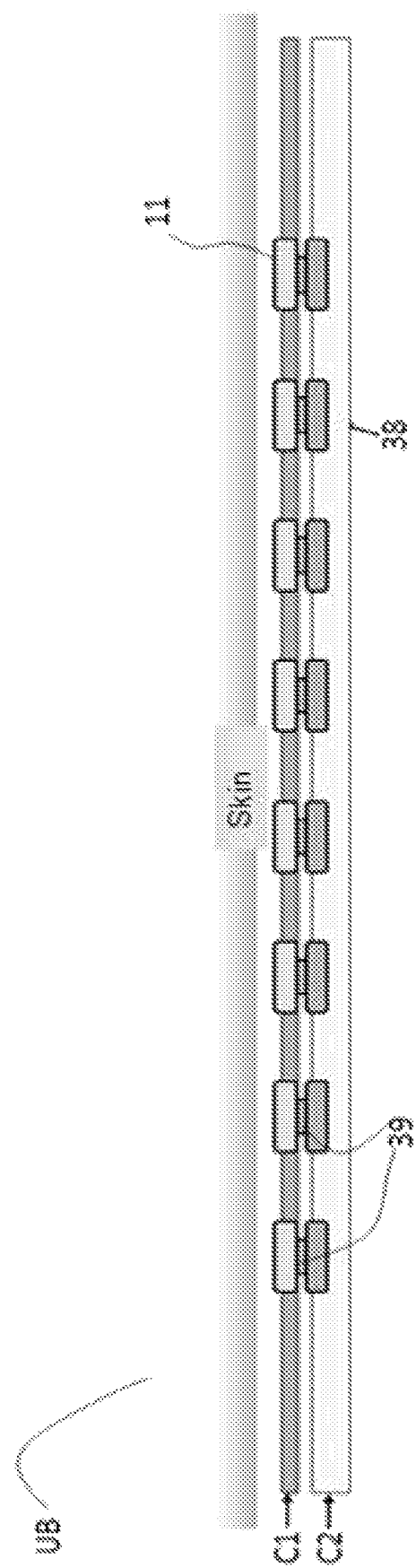
FIG. 1 is a profile view of a portable device for measuring electromyographic signals of a user according to one embodiment of the present invention.
Figure 2:
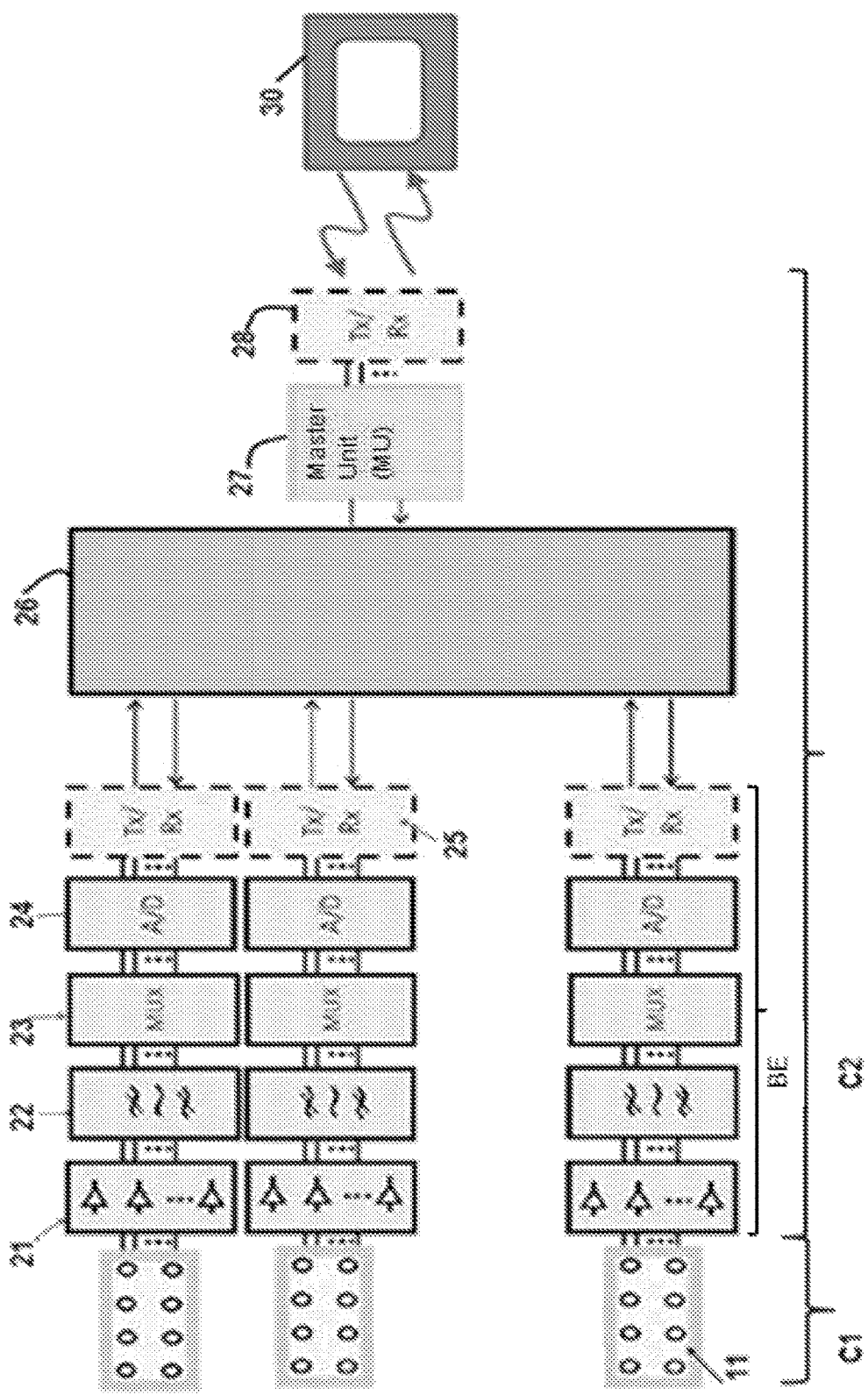
FIG. 2 is a schematic view of the different units and/or modules arranged in each of the support layers of the portable device of FIG. 1.

FIGS. 1 and 2 show therein one embodiment of a portable device for measuring electromyographic signals (or for measuring high-resolution/density electromyographic signals) of a user. Particularly, according to this embodiment, the portable device UB includes a flexible sheet support, such as a fabric, which can be incorporated in or attached to a wearable item of clothing (an armband, strap or sleeve/stocking for the arms/legs of the user, an abdominal band, a shirt etc.), integrated by two independent, overlapping layers C1, C2, attached, in a detachable manner, by means of electro-conductive couplings 39 (button, clip, etc.). Detachment of the two support layers C1, C2 is thereby readily allowed, which allows washing/cleaning and reusing the first support layer C1, which is the support layer in contact with the skin of the user while acquiring/measuring the electromyographic signals.

The first support layer C1 incorporates detection means with several electromyography sensors 11 for acquiring the electromyographic signals. According to the embodiment of FIGS. 1 and 2, the mentioned electromyography sensors 11 are made up of electrodes, preferably high-density electrodes, placed in the first support layer C1 in a matricial form. The electrodes are made of a highly conductive material and can be of the dry type or to be used with a conducting gel. The electrodes can also be of a ring type, point type, bar type, etc.

In other alternative embodiments which are not illustrated in this case, the mentioned electrodes 11 are placed in the first support layer C1 either in a laplacian form or in circular form.

The second support layer C2 incorporates all the electronics BE (means/modules/circuits, etc.) necessary for performing the conditioning of the mentioned acquired electromyographic signals, conversion of the electromyographic signals to a digital format (by means of a A/D converter 24) and transmission 25 of the conditioned and digitized electromyographic signals through a communication channel 26 to a master electronic unit 27. The master electronic unit 27 is configured for controlling said electronic means BE and to further transmit the received conditioned and digitized electromyographic signals through a guiding or wireless means 28 to a control unit 30 for monitoring thereof. That is, the master electronic unit 27 is in communication with the transmission unit 25 and with the communication channel 26 for controlling the mentioned steps of conditioning and conversion of the electromyographic signals and also to perform the transmission thereof to the control unit 30.

Figure 4:
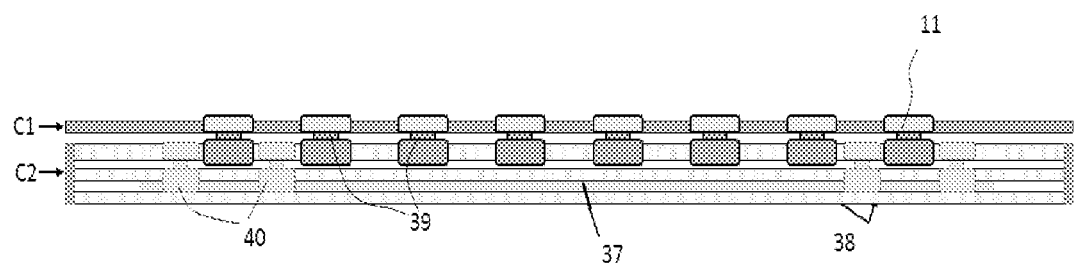
FIG. 4 illustrates one embodiment of the proposed portable device for measuring electromyographic signals of a user.
Figure 4:
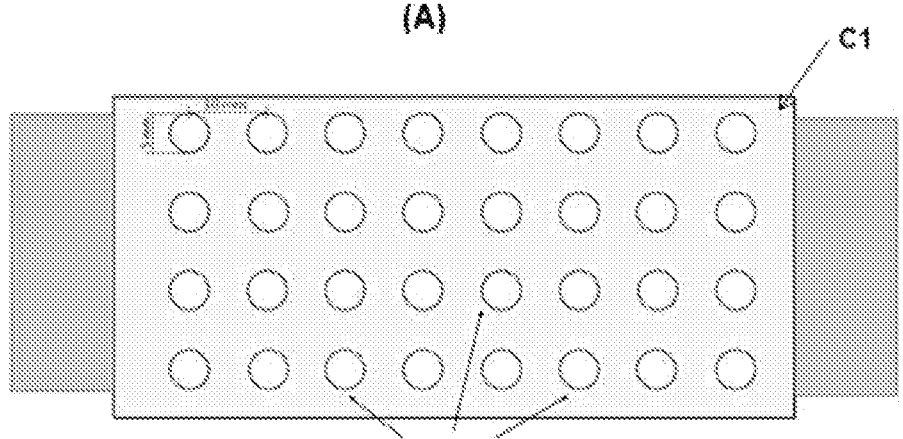

According to the invention, the communication channel 26 may be formed by a data bus 36 (see FIG. 5) or by a conductive plane formed by an electro-resistive track 37 (see FIG. 4) In this last case, electro-conductive contacts 40 will allow communication between the electronics and the plane as they are separated by an insulating material.

The mentioned control unit 30 can be arranged in the second support layer C2, or alternatively, can be remote with respect to the portable device UB. In this last case, the control unit 30 preferably comprises a computing device with one or more processors and at least one memory (for example, a PC, a laptop, a tablet, etc.) to further perform the processing of the received electromyographic signals.

The conditioning of the acquired electromyographic signals generally comprises the amplification, time filtering (optionally also spatial filtering) and optionally also the multiplexing of the acquired electromyographic signals. According to the embodiment of FIGS. 1 and 2, the mentioned conditioning of the electromyographic signals is performed by three independent electronic control units including an amplification unit 21, a filtering unit, for example a band-pass filter, 22 and a multiplexing unit 23.

Preferably, the first support layer C1 is developed in a waterproof, flexible and breathable smart fabric, whereas the second support layer C2 is also developed in a smart fabric with semiconductive properties in certain waterproof and breathable portions. The second support layer C2 furthermore includes an insulating material 38 for the insulation of the electronics incorporated therein.

Figure 5:
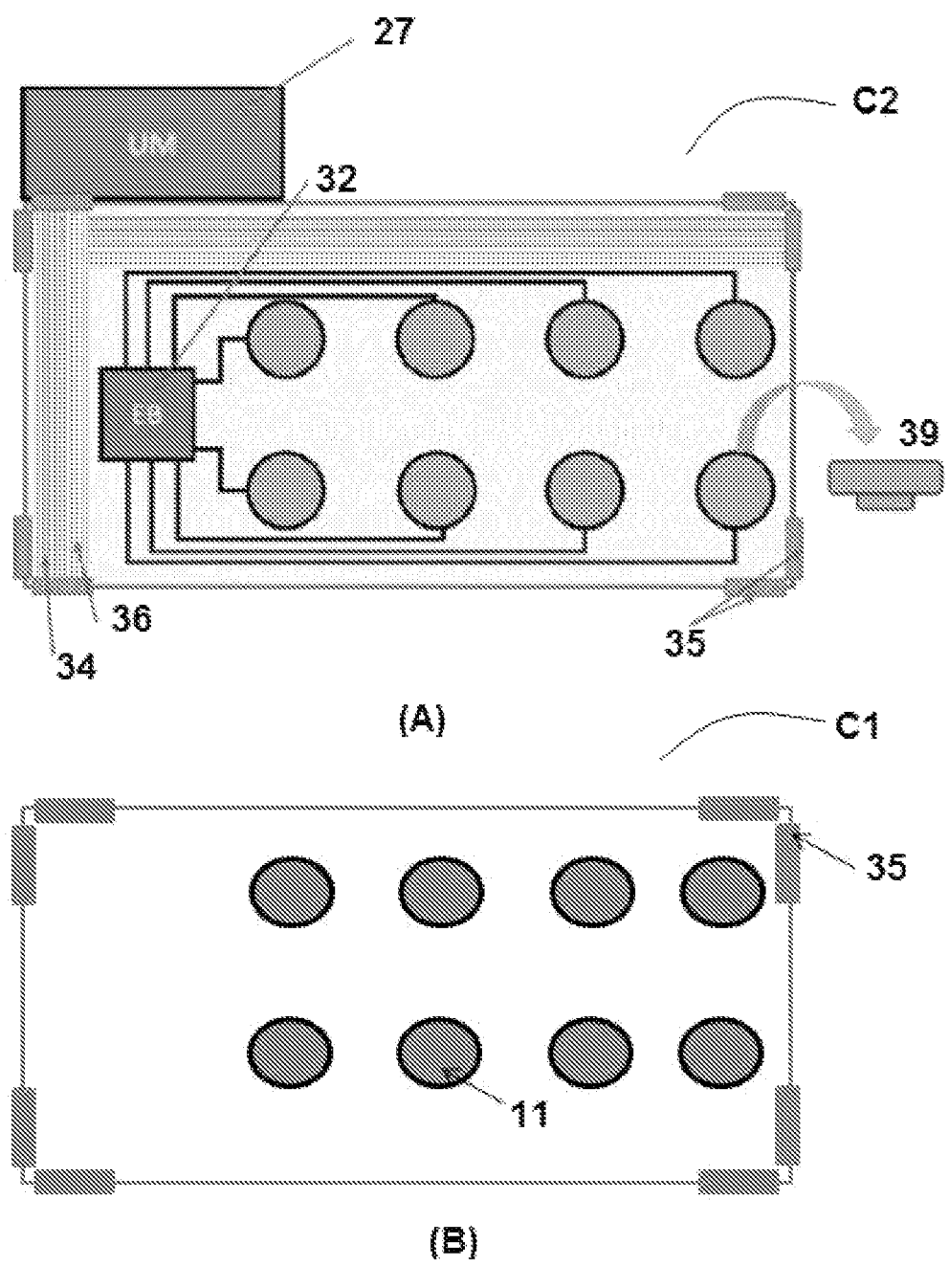
FIG. 5 illustrates another embodiment of the proposed portable device for measuring electromyographic signals of a user. In this case, the communication channel of the portable device comprises a data bus.

As indicated above, the communication channel 26 can comprise a conductive plane formed by an electro-resistive track 37 (FIG. 4) or a data bus 36 (FIG. 5). According to the present invention, the mentioned conductive plane with the electro-resistive track 37, having a certain conductivity, is obtained by applying a layer of electro-conductive paint on said plane (for example, according to the teachings described in patent application ES2346174).

According to the invention, the portable device UB can include one or more batteries for electrically powering the different electronics BE of the second support layer C2. In one embodiment, the battery (batteries) will be included in the second support layer C2, for example, close to the master electronic unit 27 and connected to all the electronic means BE by means of a power supply bus 34 or the conductive plane 37. Alternatively, the battery (batteries) may be included in a backpack or bag carried by the user while performing the exercise, a power supply wiring being envisaged from the battery (batteries) to the portable device.

Similarly, the portable device can include warning means (sounds and/or visual, for example, by means of a LED and/or a loudspeaker emitting a beeping sound), included preferably in the control unit 30, configured for emitting indications associated with changes in a prefixed muscle pattern for the user (at the start of the exercise, previous sessions, etc.), based for example on muscle co-activation indices, muscle fatigue indices, etc. obtained when processing the electromyographic signals in time, frequency or spatial domain.

Figure 3:
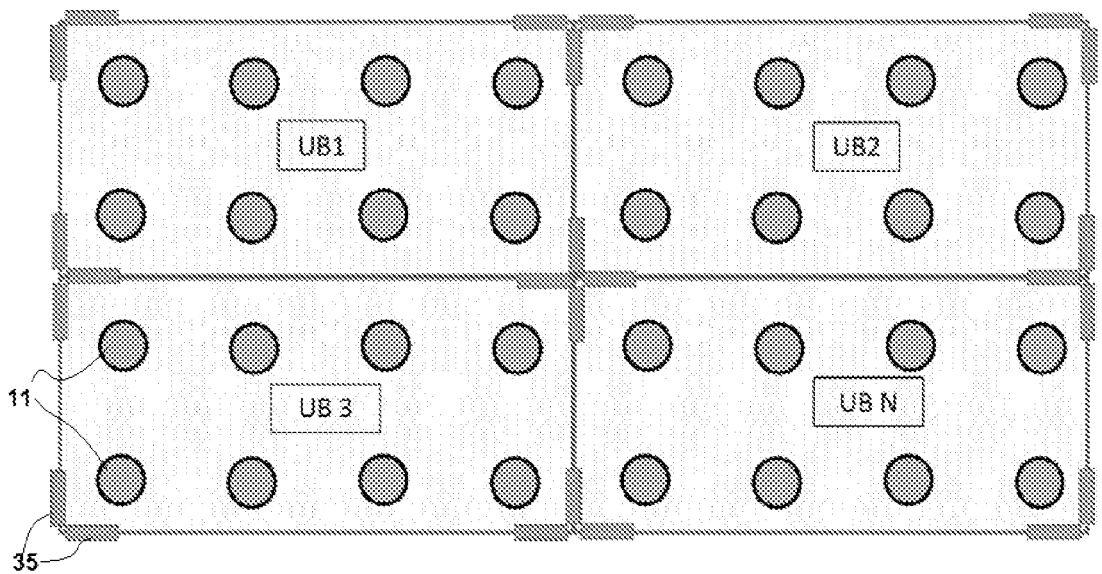
FIG. 3 is a plan view of a portable device composed of four portable devices for measuring electromyographic signals of a user according to one embodiment of the present invention. In this case, the four portable devices are attached by means of electro-conductive coupling elements, thereby increasing the number of registered channels during the measurement of the electromyographic signals of the user which allows monitoring a wider muscle area.

FIG. 3 shows therein another embodiment of the present invention in which the portable device UB for measuring the electromyographic signals is attached to other portable devices UB1 . . . UBN, thereby allowing the acquisition of electromyographic signals of a larger muscle area or areas of the user due to the increase of the number of acquisition channels (N×n electromyographic signals). The different portable devices UB1 . . . UBN are mechanically and electrically coupled or attached to one another along their periphery by means of electro-conductive coupling elements 35. In this case, the control unit 30 is configured to monitor the electromyographic signals received from the master electronic units 27 of all the coupled portable devices UB1 . . . UBN.

Figure 6:
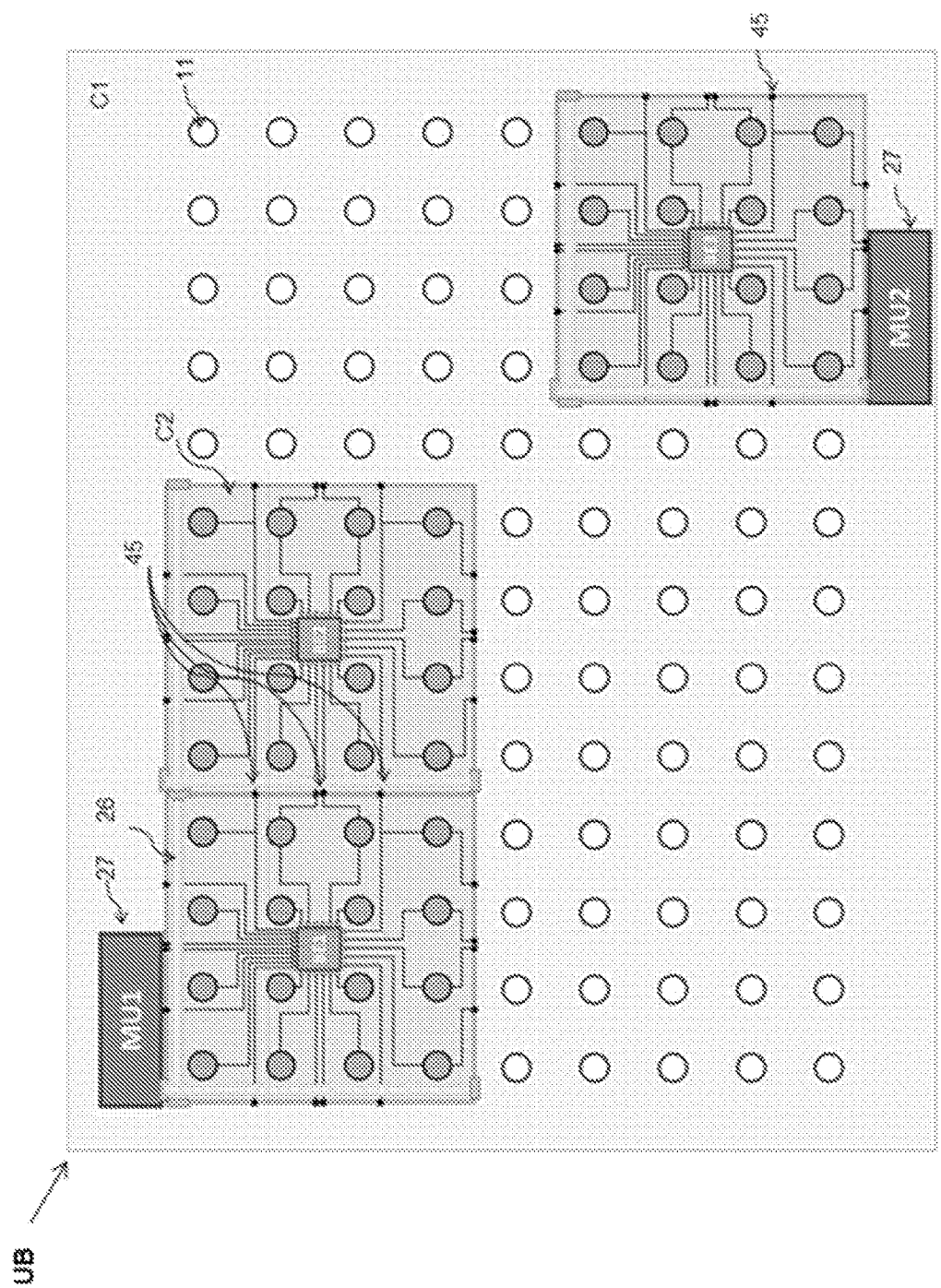
FIG. 6 illustrates another embodiment of the proposed portable device. In this case, the device comprises more a plurality of second support layers each one being mechanically and electrically attached in a detachable manner to the first support layer.

With reference now to FIG. 6, therein it is illustrated another embodiment of the proposed portable device UB. In this case, the device comprises a plurality of second support layers C2 each being mechanically and electrically attached in a detachable manner to the first support layer C1. As may be seen in the figure, two (not limitative) of the plurality of second support layers C2 are mechanically and electronically attached to each other, i.e. interconnected (sharing the master control unit 27), to increase the detection area and to exchange both analog and digitized information by electrical connectors 45 and communication channel 26, whereas another second support layer C2 (it could also be more than one) is placed remote to the two interconnected second support layers C2 including its own master control unit 27. The master electronic unit 27 of the two interconnected second support layers C2 is in this case configured for controlling each one of the electronic means BE of the two interconnected second support layers C2. Besides, the control unit 30 can monitor the electromyographic signals received from all the master electronic units 27 of the portable device UB (the one shared between interconnected second support layers C2 and the one from the remote second support layer C2).

In the embodiment of FIG. 6 the first support layer C1 is preferably incorporated in or attached to a wearable item of clothing including an armband, a strap for an upper or lower limb of the body of the user, an abdominal band, a trousers or a shirt, and the plurality of second support layers C2 (interconnected and/or remotes) are configured to be attached to different parts of said wearable item of clothing selected depending on the muscle or muscles from which the electromyographic signals have to be measured according to the interest of the exercise carried out by the user.

Figure 7:
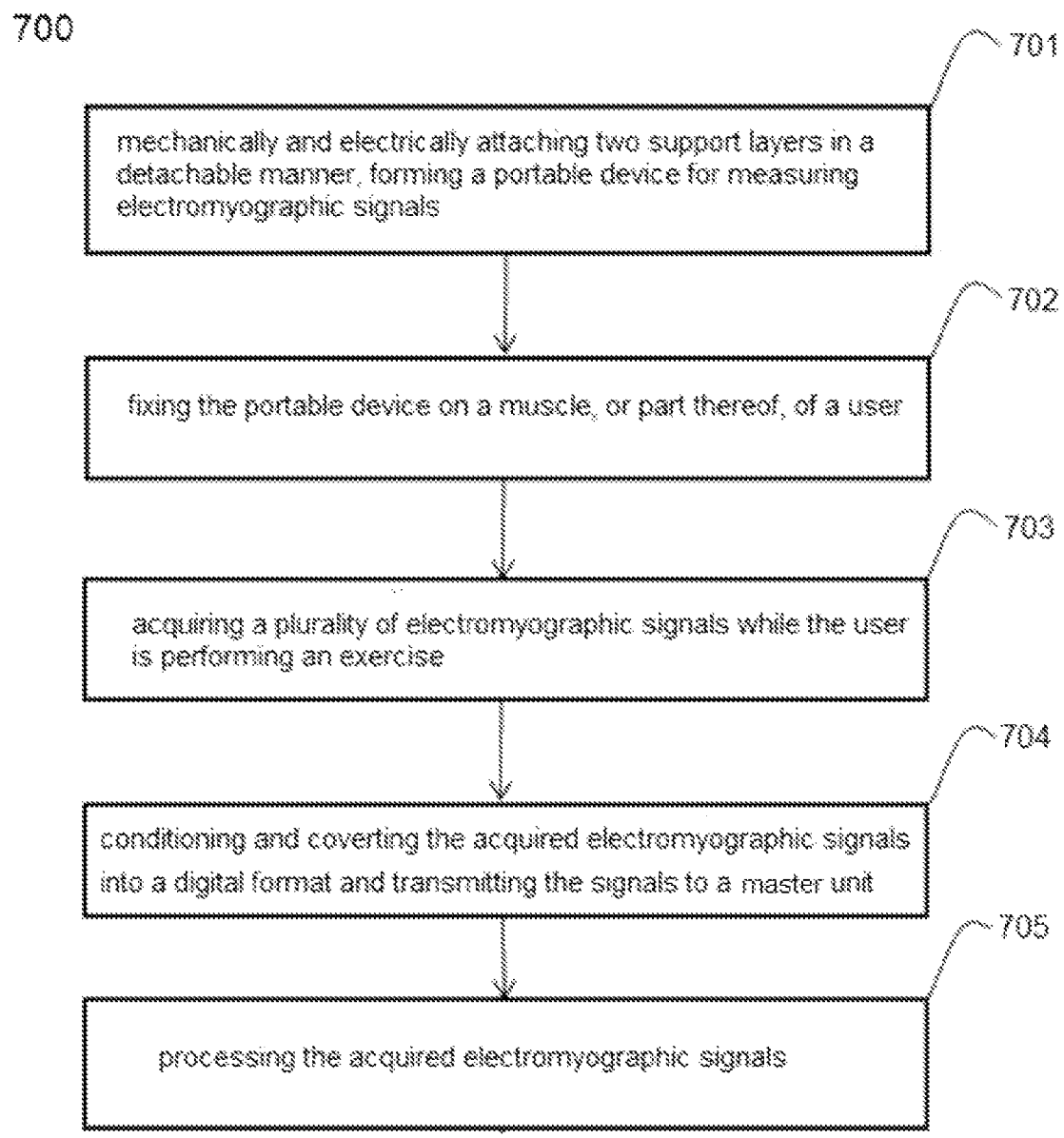
FIG. 7 is a flow diagram illustrating an example of a method for measuring electromyographic signals of a user according to one embodiment of the present invention.

FIG. 7 shows therein one embodiment of a method 700 proposed for measuring electromyographic signals of a user using the portable device or portable devices described above.

The method 700 includes step 701 of mechanically and electrically attaching the first support layer C1 with one or more second support layers C2 forming the proposed portable device UB, in a detachable manner, by means of the mentioned electro-conductive couplings 39. The portable device UB is then fixed (step 702) on a muscle, or on a muscle area, of the user, the first support layer C1 being in contact with the skin of the user, for monitoring same; then, a plurality of electromyographic signals are acquired (step 703) by the electrodes 11 of the first support layer C1 while the user is performing an exercise. Once the electromyographic signals have been acquired, conditioned and converted to a digital format by the electronic means BE, they are transmitted, by the master control unit 27, to the control unit 30 (step 704) for processing thereof (step 705). In this case, the control unit 30 comprises a computing device such as a PC, a laptop, a tablet, among others possible computing devices which allow signal processing.

In the proposed method, in case of having more than one second support layers C2, these can be attached to each other by electrical connectors 45 (see FIG. 6) and can exchange both analog and digitized information via said electrical connectors 45 and communication channel 26, e.g. to cover different muscles of a same body part. Besides, in case of having more than one second support layers C2, these can also be remote to each other, e.g. to cover muscles of different body parts, comprising each remote second support layer C2 an own master electronic unit 27.

In one embodiment, the result obtained in the processing step is shown to the user, either through a display of the computing device itself or through a portable communication device of the user him/herself, for example a smartphone or tablet. In this last case, the computing device will communicate the result obtained in the processing step to the actual portable communication device of the user.

Displaying the results to the user (biofeedback) during or at the end of the exercise, will allow controlling the performance of the exercise in order to better perform same, such that the user can put greater emphasis on the muscle or muscle area which is being treated or in which a deficiency/disorder has been detected. A greater change at the neuromuscular level can thereby be favored rapidly, whereby help is provided in the learning of certain technical gestures or movements necessary in different sports activities, as well as the better performance of repetitive, isokinetic or isometric contractions exercises, among others, during rehabilitation, diagnosis or training processes.

The electromyographic signals can be processed at the same time as performing the exercise or can be processed offline (prior storage in the computing device, for example, in a memory thereof), it can comprise, among others calculations, calculation of one or more muscle activation maps and/or calculation of different indices relating to muscle coordination, activation and fatigue of the user in relation to the muscle or a monitored muscle area.

In one embodiment, the mentioned muscle activation map or maps and/or calculation of said indices is calculated, without it being limited, according to the teachings disclosed in the scientific articles "Identification of isometric contractions based on High Density EMG maps, Journal of Electromyography and Kinesiology 2012" and "High-density surface EMG maps from upper-arm and forearm muscles, Journal of NeuroEngineering and Rehabilitation 2012" of the same inventors as the present invention.

The scope of the present invention is defined in the attached claims.

The invention claimed is:

1. A portable device for measuring a plurality of electromyographic signals of a user, said portable device comprising:
  a first support layer comprising detection means including a plurality of electrodes configured to be arranged, in use, in contact with skin of the user on at least one muscle, or part thereof, and configured to acquire the plurality of electromyographic signals, said first support layer being incorporated in or attached to a wearable item of clothing including an armband, a strap for an upper or lower limb of a body of the user, an abdominal band, a trousers or a shirt;
  a plurality of second support layers mechanically and electrically attached in a detachable manner to the first support layer by means of electro-conductive couplings;
  a first master electronic unit;
  each second support layer of the plurality of second support layers including an electronic module that comprises: an amplification unit, a filtering unit and a multiplexing unit to condition the plurality of a electromyographic signals, an A/D converter to convert the plurality of electromyographic signals to a digital format, and a transmission unit to transmit the conditioned and digitized plurality of electromyographic signals to the first master electronic unit through a communication channel;
  the plurality of second support layers further being mechanically and electronically attached to each other, through electrical connectors and the communication channel, to exchange both analog and digitized information, and sharing the first master electronic unit; and
  the first master electronic unit is configured to control each electronic module of each second support layer of the plurality of second support layers and to transmit the conditioned and digitized plurality of electromyographic signals to a control unit for monitoring thereof.

2. The device according to claim 1, further comprising at least one additional second support layer mechanically and electrically attached in a detachable manner to the first support layer by means of electro-conductive couplings, the at least one additional second support layer being remote from the plurality of second support layers and comprising a second master electronic unit, wherein the control unit is configured to monitor the plurality of electromyographic signals received from the first master electronic unit and from the second master electronic unit.

3. The device according to claim 1, further comprising in a periphery electro-conductive coupling elements to be mechanically and electrically coupled to one or more portable devices to increase an electromyographic signal detection area, wherein the control unit is configured to monitor the plurality of electromyographic signals received from the first master electronic unit.

4. The device according to claim 1, wherein the control unit is an electronic unit positioned in a second support layer of the plurality of second support layers.

5. The device according to claim 1, further comprising at least one battery to electrically power the electronic module of each second support layer of the plurality of second support layers.

6. The device according to claim 4, further comprising a warning unit, embedded in the control unit, configured to emit indications associated with changes in a prefixed muscle pattern, based at least on muscle co-activation or fatigue indices, the muscle co-activation or fatigue indices being obtained during a processing of the plurality of electromyographic signals previously performed in a time, frequency or spatial domain, the warning unit including at least one of a Light Emitting Diode or a loudspeaker.

* * * * *